(12) United States Patent
Shintou et al.

(10) Patent No.: US 9,650,367 B2
(45) Date of Patent: May 16, 2017

(54) COMPOUND, AND INK, COLOR FILTER RESIST COMPOSITION, THERMAL TRANSFER RECORDING SHEET AND TONER CONTAINING THE SAME

(71) Applicant: CANON KABUSHIKI KAISHA, Tokyo (JP)

(72) Inventors: Taichi Shintou, Saitama (JP); Masao Nakano, Kamakura (JP); Koromo Shirota, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/130,673

(22) Filed: Apr. 15, 2016

(65) Prior Publication Data

US 2016/0304508 A1    Oct. 20, 2016

(30) Foreign Application Priority Data

Apr. 17, 2015 (JP) .................................. 2015-085299

(51) Int. Cl.
| | |
|---|---|
| C07D 417/06 | (2006.01) |
| C09D 11/037 | (2014.01) |
| G03F 7/00 | (2006.01) |
| G03G 9/09 | (2006.01) |
| B41M 5/385 | (2006.01) |
| B41M 5/39 | (2006.01) |

(52) U.S. Cl.
CPC ......... *C07D 417/06* (2013.01); *B41M 5/3854* (2013.01); *B41M 5/39* (2013.01); *C09D 11/037* (2013.01); *G03F 7/0007* (2013.01); *G03G 9/09* (2013.01); *B41M 2205/02* (2013.01); *B41M 2205/30* (2013.01)

(58) Field of Classification Search
CPC .................................................... C07D 417/06
See application file for complete search history.

(56) References Cited

U.S. PATENT DOCUMENTS

| | | | | |
|---|---|---|---|---|
| 4,891,354 A | * | 1/1990 | Evans ................. | B41M 5/3854 428/480 |
| 6,107,487 A | * | 8/2000 | Blum ...................... | B41J 31/00 428/913 |
| 7,553,797 B2 | * | 6/2009 | Ono ..................... | B41M 5/3854 428/32.6 |

FOREIGN PATENT DOCUMENTS

| | | |
|---|---|---|
| JP | 2012-213885 A | 11/2012 |
| JP | 2012-214575 A | 11/2012 |
| WO | 92-19684 A1 | 11/1992 |

* cited by examiner

*Primary Examiner* — Laura L. Stockton
(74) *Attorney, Agent, or Firm* — Canon U.S.A., Inc., IP Division

(57) ABSTRACT

A lightfast orange color compound is provided. The compound has a structure including a pyrazolone ring and a thiazole ring that are bound to each other.

9 Claims, No Drawings

COMPOUND, AND INK, COLOR FILTER RESIST COMPOSITION, THERMAL TRANSFER RECORDING SHEET AND TONER CONTAINING THE SAME

BACKGROUND

Field of the Disclosure

The present disclosure relates to a compound, an ink, a color filter resist composition, a thermal transfer recording sheet, and a toner.

Description of the Related Art

With the spread of portable color display devices, the demand is rapidly increasing for easy color printing of photographs and documents taken or prepared with such devices. Color printing methods responding to this demand include electrophotographic, ink jet, and thermal transfer recording methods.

Color filters are necessary to display color images on liquid crystal display devices and are a type of important components involved in the performance of liquid crystal display devices. It is known that color filters are manufactured by a dyeing method, a printing method, an ink jet method, or a photoresist method. In particular, the photoresist method facilitates the control of spectral characteristics and color reproducibility and allows high-definition patterning because of high resolution, and is thus the mainstream of the manufacture of color filters. The photoresist method generally uses pigments as a coloring agent. Pigments however have disadvantages, such as causing depolarization (canceling polarization), reducing the contrast of color images on the liquid crystal display device, reducing the lightness of the color filter, and being required to be stably dispersed in an organic solvent or a polymer. The thermal transfer recording method allows printing in a dry process, and the printer using this method can be downsized and portable. Thus, the thermal transfer recording method is advantageous as an easy printing method independent of surrounding environment. In the thermal transfer recording method, the dye contained in transfer sheets and inks for the transfer sheet affects the transfer recording speed and the image quality and storage stability of recorded articles and is thus important material. Although pigments are typical coloring agents in color toners, it is reported that a dye is used to increase color developability. Textile printing using an ink jet method has recently received attention as a method capable of providing printed textiles with low energy consumption and low cost. Although ink jet inks for textile printing may contain a pigment, it is reported that a dye is used to increase color developability.

Known dyes used as coloring agent in these fields include azo dyes and methine dyes (Japanese Patent Laid-Open Nos. 2012-214575 and 2012-213885). Unfortunately, dyes are generally inferior in light fastness. Lightfast dyes are desired.

SUMMARY OF THE DISCLOSURE

The present disclosure provides a lightfast orange color compound.

The present disclosure also provides a lightfast ink, a lightfast color filter resist composition, a lightfast thermal transfer recording sheet, and a lightfast toner.

Accordingly, the following compound is provided.

The compound has a structure expressed by the following general formula (1).

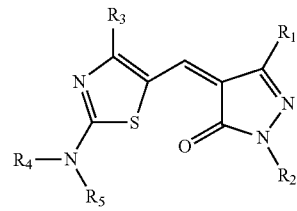

formula (1)

In general formula (1), $R_1$ represents a group selected from the group consisting of alkyl group, aryl group, aryl group having a substituent, acyl group, carboxy group, alkoxycarbonyl group, carboxamide group, amino group, and cyano group; $R_2$ represents a group selected from the group consisting of alkyl group, aryl group, and aryl group having a substituent; $R_3$ represents a group selected from the group consisting of alkyl group, aryl group, aryl group having a substituent, and heterocyclic group; and $R_4$ and $R_5$ each independently represent alkyl group. The substituents of $R_1$ to $R_3$ are each one selected from the group consisting of alkyl group, alkoxy group, and sulfonic acid salt group.

According to another aspect of the present disclosure, an ink containing the above compound is provided.

Also, a color filter resist composition containing the compound is provided.

Also, a thermal transfer recording sheet containing the compound is provided.

Furthermore, a toner containing the compound is provided.

Further features of the present disclosure will become apparent from the following description of exemplary embodiments.

DESCRIPTION OF THE EMBODIMENTS

The subject matter of the disclosure will be further described in detail. The present inventors have found through their intensive research that compounds (hereinafter referred to as the present compound) having a structure expressed by the following general formula (1) have a highly lightfast orange color. In addition, the inventors have found that the use of present compound can provide a lightfast ink, a lightfast color filter resist composition, a lightfast thermal transfer recording sheet, and a lightfast toner.

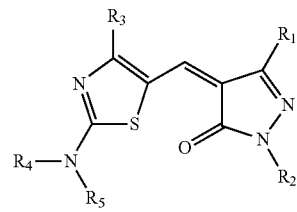

In general formula (1), $R_1$ represents a group selected from the group consisting of alkyl group, aryl group, aryl group having a substituent, acyl group, carboxy group, alkoxycarbonyl group, carboxamide group, amino group, and cyano group; $R_2$ represents a group selected from the group consisting of alkyl group, aryl group, and aryl group having a substituent; $R_3$ represents a group selected from the group consisting of alkyl group, aryl group, aryl group having a substituent, and heterocyclic group; and $R_4$ and $R_5$ each independently represent alkyl group. The substituents of $R_1$ to $R_3$ are each one selected from the group consisting of alkyl group, alkoxy group, and sulfonic acid salt group.

The compound having the structure expressed by general formula (1) will first be described.

Examples of the alkyl group represented by $R_1$ in general formula (1) include, but are not limited to, saturated or unsaturated linear, branched, or cyclic primary to tertiary alkyl groups having a carbon number of 1 to 20, such as methyl, ethyl, n-propyl, iso-propyl, n-butyl, sec-butyl, tert-butyl, octyl, dodecyl, nonadecyl, cyclobutyl, cyclopentyl, cyclohexyl, methylcyclohexyl, 2-ethylpropyl, 2-ethylhexyl, and cyclohexenylethyl. In particular, when $R^1$ is the methyl group, the compound is a lightfast orange color compound and is thus advantageous.

The aryl group represented by $R_1$ in general formula (1) may be substituted or unsubstituted. If the aryl group is substituted, the substituent may be alkyl, alkoxy, or a sulfonic acid salt group. More specifically, examples of the aryl group include phenyl, naphthyl, methylphenyl, methoxyphenyl, and phenyl sulfonic acid salt. In particular, when $R^1$ is a substituted or unsubstituted phenyl group, the compound is a lightfast orange color compound and is thus advantageous.

The acyl group represented by $R_1$ in general formula (1) may be, but is not limited to, acetyl, propionyl, or benzoyl.

The alkoxycarbonyl group represented by $R_1$ in general formula (1) may be, but is not limited to, methoxycarbonyl, ethoxycarbonyl, or propoxycarbonyl.

The carboxamide group represented by $R_1$ in general formula (1) may be, but is not limited to, carboxylic acid dimethylamide, carboxylic acid diethylamide, carboxylic acid methylamide, or carboxylic acid ethylamide.

Examples of the amino group represented by $R_1$ in general formula (1) include, but are not limited to, dialkylamino groups, such as dimethylamino, diethylamino, dipropylamino, and dibutylamino; monoalkylamino groups, such as methylamino, ethylamino, propylamino, and butylamino; and diphenylamino and phenylamino.

Examples of the alkyl group represented by $R_2$ in general formula (1) include, but are not limited to, saturated or unsaturated linear, branched, or cyclic primary to tertiary alkyl groups having a carbon number of 1 to 20, such as methyl, ethyl, n-propyl, iso-propyl, n-butyl, sec-butyl, tert-butyl, octyl, dodecyl, nonadecyl, cyclobutyl, cyclopentyl, cyclohexyl, methylcyclohexyl, 2-ethylpropyl, 2-ethylhexyl, and cyclohexenylethyl. In particular, when $R^2$ is the methyl group, the compound is a lightfast orange color compound and is thus advantageous.

The aryl group represented by $R_2$ in general formula (1) may be substituted or unsubstituted. If the aryl group is substituted, the substituent may be alkyl, alkoxy, or a sulfonic acid salt group. More specifically, examples of the aryl group include phenyl, naphthyl, methylphenyl, methoxyphenyl, and phenyl sulfonic acid salt. In particular, when $R^2$ is a substituted or unsubstituted phenyl group, the compound is a lightfast orange color compound and is thus advantageous.

Examples of the alkyl group represented by $R_3$ in general formula (1) include, but are not limited to, saturated or unsaturated linear, branched, or cyclic primary to tertiary alkyl groups having a carbon number of 1 to 20, such as methyl, ethyl, n-propyl, iso-propyl, n-butyl, sec-butyl, tert-butyl, octyl, dodecyl, nonadecyl, cyclobutyl, cyclopentyl, cyclohexyl, methylcyclohexyl, 2-ethylpropyl, 2-ethylhexyl, and cyclohexenylethyl. In particular, when $R^3$ is the methyl group, the compound is a lightfast orange color compound and is thus advantageous.

The aryl group represented by $R_3$ in general formula (1) may be substituted or unsubstituted. If the aryl group is substituted, the substituent may be alkyl, alkoxy, or a sulfonic acid salt group. More specifically, examples of the aryl group include phenyl, naphthyl, methylphenyl, methoxyphenyl, and phenyl sulfonic acid salt. In particular, when $R^3$ is a substituted or unsubstituted phenyl group, the compound is a lightfast orange color compound and is thus advantageous.

The heterocycle represented by $R_3$ in general formula (1) may be, but is not limited to, pyridyl or thienyl.

Examples of the alkyl group represented by $R_4$ or $R_5$ include, but are not limited to, saturated or unsaturated linear, branched, or cyclic primary to tertiary alkyl groups having a carbon number of 1 to 20, such as methyl, ethyl, n-propyl, iso-propyl, n-butyl, sec-butyl, tert-butyl, octyl, dodecyl, nonadecyl, cyclobutyl, cyclopentyl, cyclohexyl, methylcyclohexyl, 2-ethylpropyl, 2-ethylhexyl, and cyclohexenylethyl.

An exemplary process for producing the present compound having the structure expressed by general formula (1) will now be described. The method for producing the present compound is however not limited to this process.

$R_1$ to $R_5$ of the present compound in the following reaction formulas and general formula (2) are the same as in the above description. The structure expressed by general formula (1) has a cis-trans isomer expressed by general formula (2) as below, and this isomer is also within the scope of the disclosure.

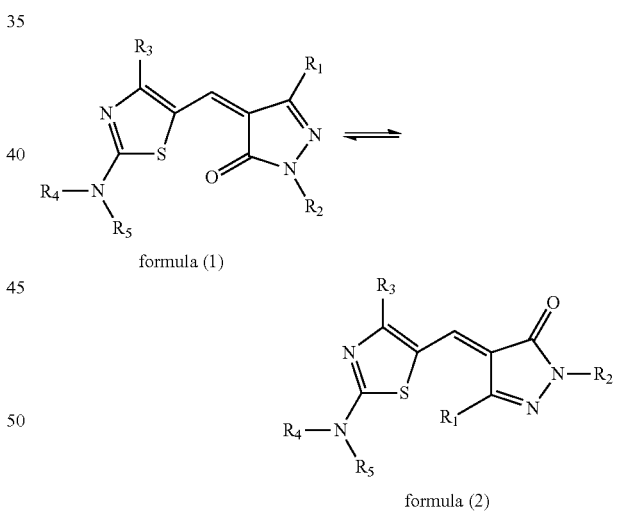

The compound expressed by general formula (1) can be easily produced from an ester compound (A).

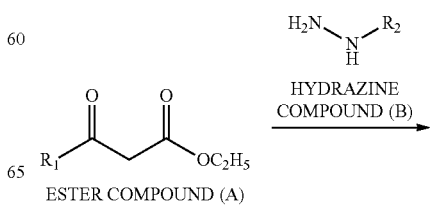

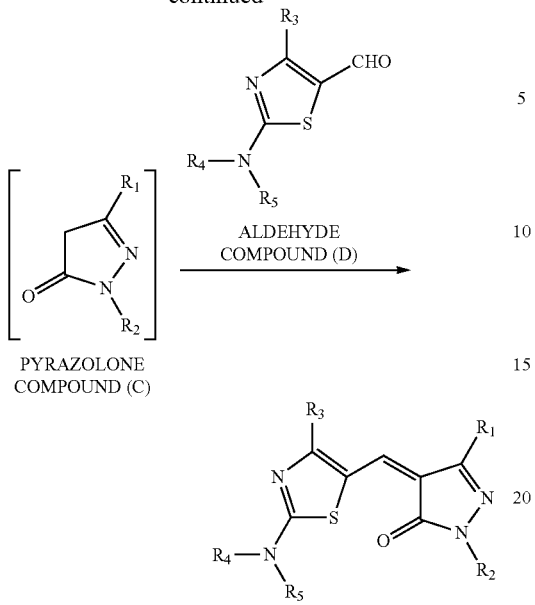

More specifically, the ester compound (A) is allowed to react with a hydrazine compound (B) to yield a pyrazolone compound (C). The pyrazolone compound (C), remaining in the reaction vessel without being taken out, is continuously allowed to react with an aldehyde compound (D) to yield a compound of general formula (1).

This reaction may be performed, for example, with reference to a known method disclosed in Journal of Medicinal Chemistry, Vol. 44, No. 22, pp. 3730-3745 (2001).

The ester compound (A) and the hydrazine compound (B) are commercially available. Also, the hydrazine compound (B) may be synthesized by a known process (for example, according to Experimental Chemistry Lecture 14. Synthesis and Reactions of Organic Compounds [III] (in Japanese), pp. 1573-1584). Examples of the hydrazine compound (C) include, but are not limited to, methylhydrazine, ethylhydrazine, n-propylhydrazine, isopropylhydrazine, n-butylhydrazine, isobutylhydrazine, sec-butylhydrazine, tert-butylhydrazine, cyclopropylhydrazine, cyclobutylhydrazine, cyclopentylhydrazine, phenylhydrazine, phenethylhydrazine, naphthylhydrazine, and benzylhydrazine.

The reaction of the above reaction formula may be performed without using a solvent, but desirably in the presence of a solvent. Any solvent that does not inhibit the reaction may be used without particular limitation, and examples thereof include water; alcohols, such as methanol, ethanol, and propanol; esters, such as methyl acetate, ethyl acetate, and propyl acetate; ethers, such as diethyl ether, tetrahydrofuran, and dioxane; aromatic hydrocarbons, such as benzene, toluene, and xylene; amides, such as N,N-dimethylformamide and N,N-dimethylimidazolidinone; nitriles, such as acetonitrile and propionitrile; and acids, such as hydrochloric acid, formic acid, acetic acid, and propionic acid. Two or more of these solvents may be mixed for use. In this case, the mixing ratio is arbitrary. The amount of the solvent to be used may be 0.1 to 1000 times the mass of the ester compound (A), and is desirably 0.5 to 100 times, such as 1.0 to 20 times.

The reaction is performed at a temperature in the range of −80° C. to 250° C., and desirably at a temperature in the range of −50° C. to 200° C., such as −20° C. to 150° C. The reaction is normally completed within 24 hours.

After the completion of this reaction, an aldehyde compound (D) is added.

The aldehyde compound (D) may be synthesized with reference to a known process disclosed in International Publication No. WO92/19684.

Examples of the aldehyde compound (D) include, but are not limited to, the following aldehyde compounds (1) to (8):

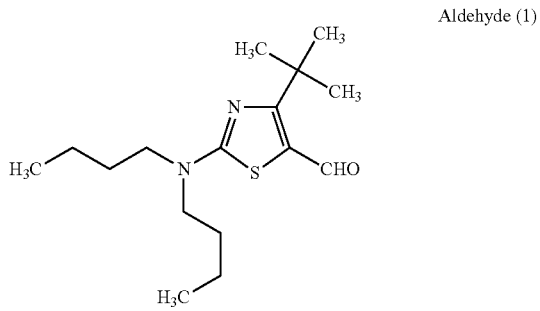

Aldehyde (1)

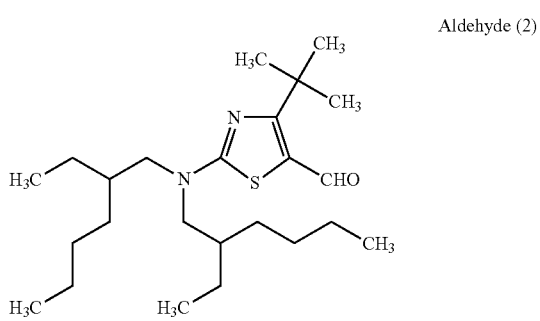

Aldehyde (2)

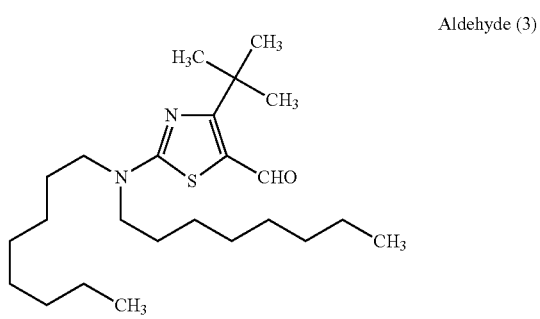

Aldehyde (3)

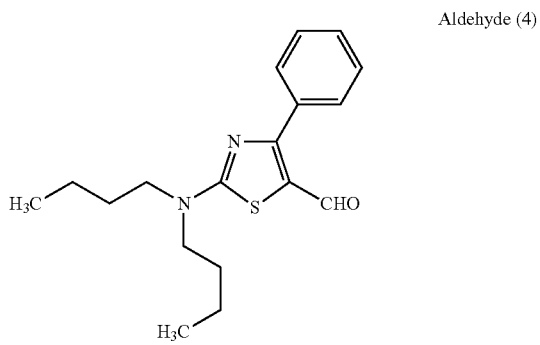

Aldehyde (4)

Aldehyde (5)

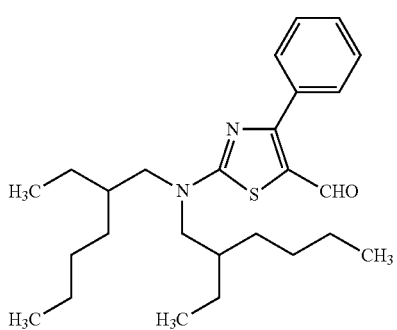

Aldehyde (6)

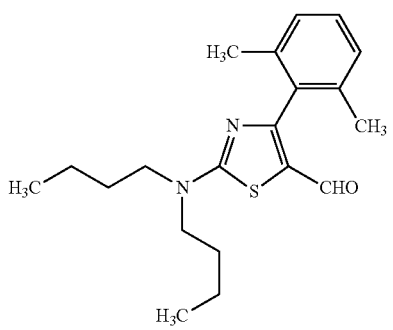

Aldehyde (7)

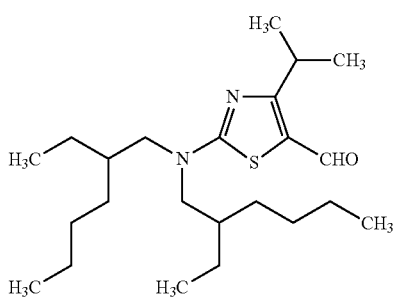

Aldehyde (8)

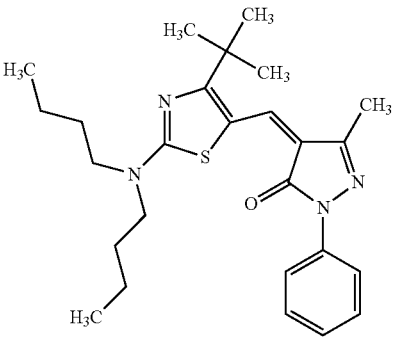

When the aldehyde compound (D) is added, it is advantageous to use an acid or a base. The use of an acid or a base helps the reaction proceed.

Examples of such an acid include inorganic acids, such as hydrochloric acid, sulfuric acid, and phosphoric acid; and organic acids, such a p-toluenesulfonic acid, formic acid, acetic acid, propionic acid, and trifluoroacetic acid. An ammonium salt of such an organic acid may be used, such as ammonium formate and ammonium acetate. Among these, p-toluenesulfonic acid, ammonium formate and ammonium acetate are advantageous. The proportion of the acid or salt thereof used is may be 0.01% to 20% by mass, desirably 0.1% to 5% by mass, relative to the aldehyde compound (D).

Examples of the base include organic bases, such as pyridine, 2-methylpyridine, diethylamine, diisopropylamine, triethylamine, phenylethylamine, isopropylethylamine, methylaniline, 1,4-diazabicyclo[2.2.2]octane (DABCO), tetrabutylammonium hydroxide, 1,8-diazabicyclo[5.4.0]undecene (DBU), and potassium acetate; organic metals, such as n-butyllithium and tert-butylmagnesium chloride; inorganic bases, such as sodium borohydride, metallic sodium, potassium hydride, and calcium oxide; and metal alkoxides, such as potassium tert-butoxide, sodium tert-butoxide, and sodium ethoxide. Among these, triethylamine and pyridine, particularly, triethylamine, are advantageous. The proportion of the base used is may be 0.1% to 20% by mass, desirably 0.2% to 5% by mass, relative to the aldehyde compound (D).

The resulting present compound is subjected to aftertreatment by a known process, and then purified to yield a highly pure compound by, for example, liquid separation, recrystallization, reprecipitation, column chromatography, or the like.

The resulting present compound may be used singly, or in combination with another compound to adjust the color according to the use. In addition, two or more pigments or dyes may be used in combination.

Examples of the present compound include, but are not limited to, the following compounds (1) to (26):

Compound (1)

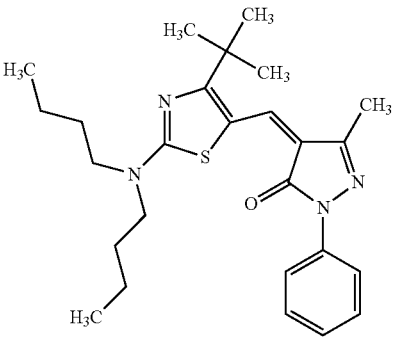

Compound (2)

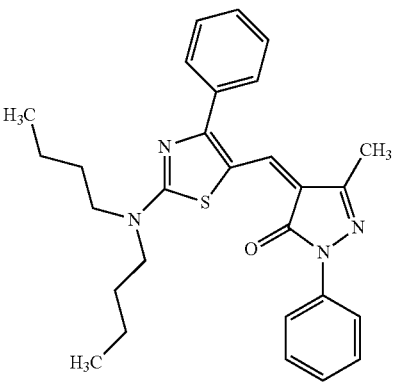

Compound (3)
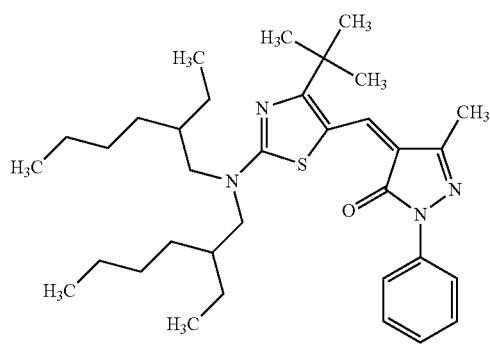
Compound (4)
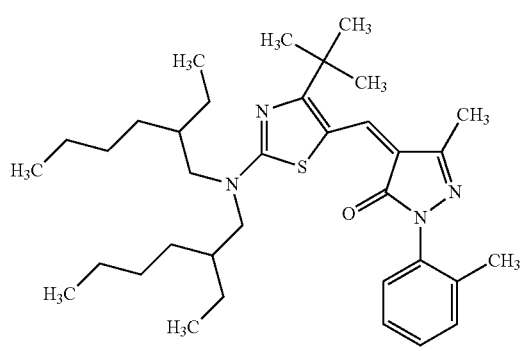
Compound (5)
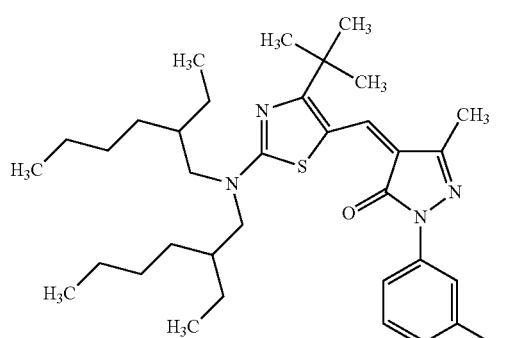
Compound (6)
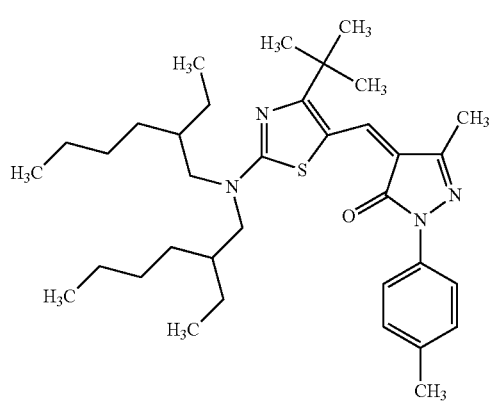
Compound (7)
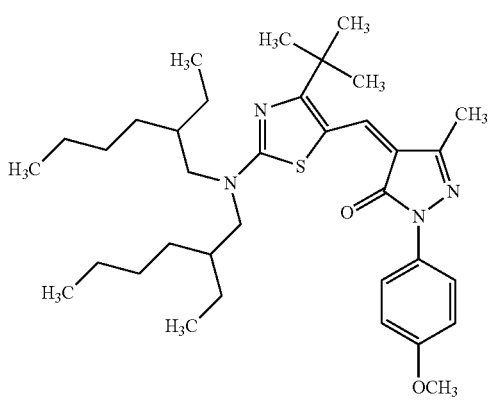
Compound (8)
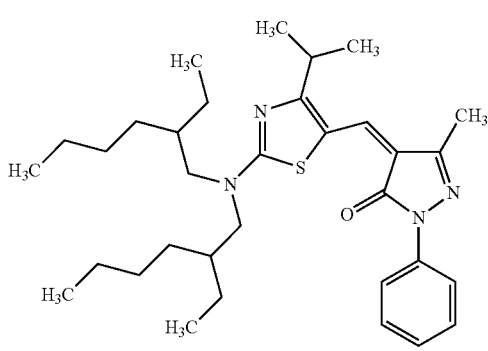
Compound (9)
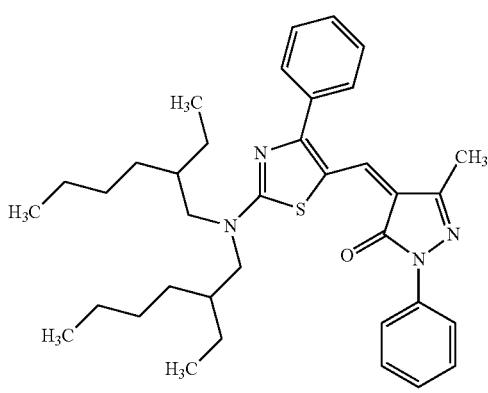
Compound (10)
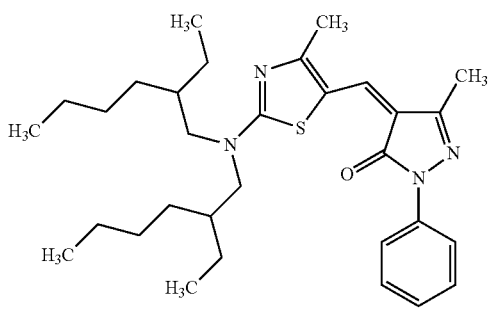

-continued
Compound (11)
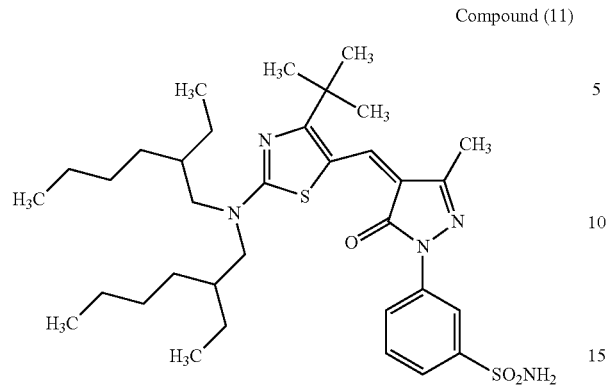
Compound (12)
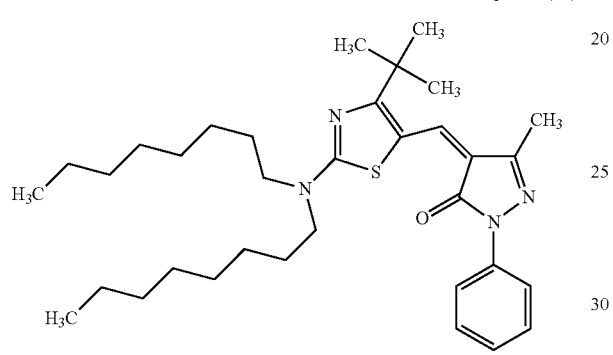
Compound (13)
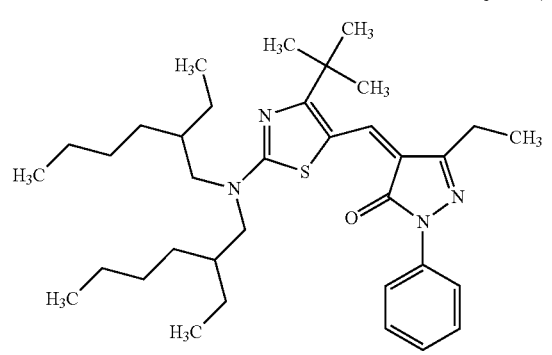
Compound (14)
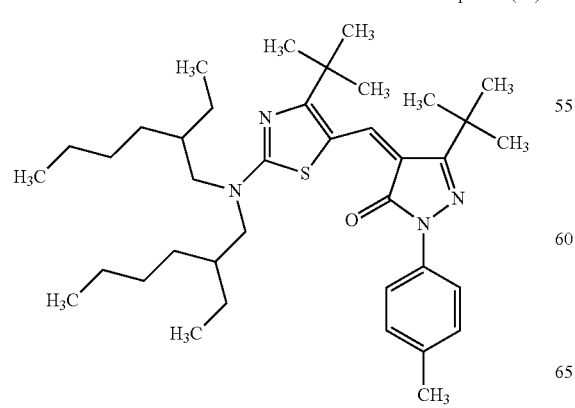
Compound (15)
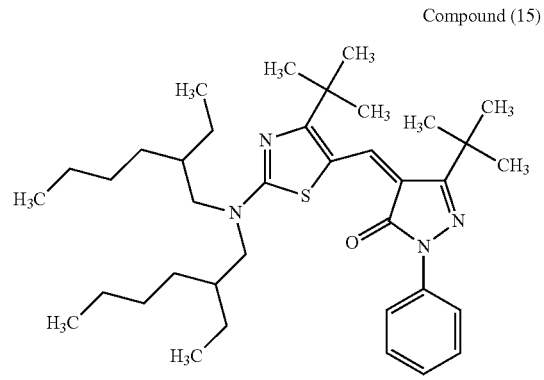
Compound (16)
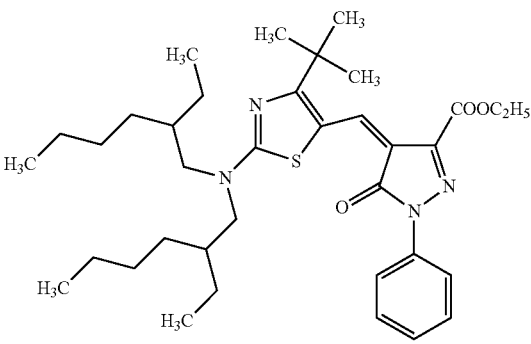
Compound (17)
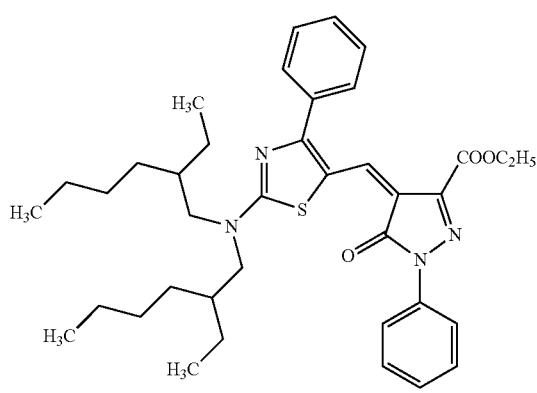
Compound (18)
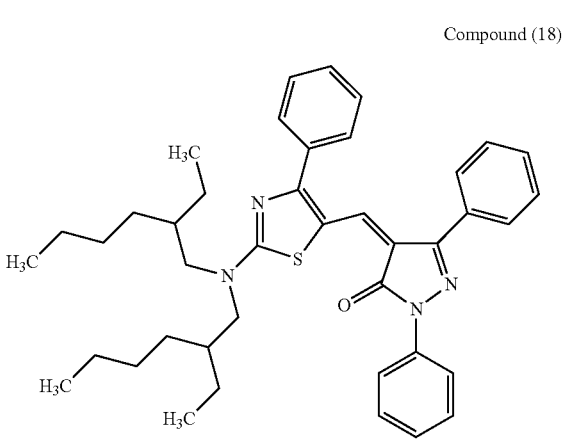

Compound (19)
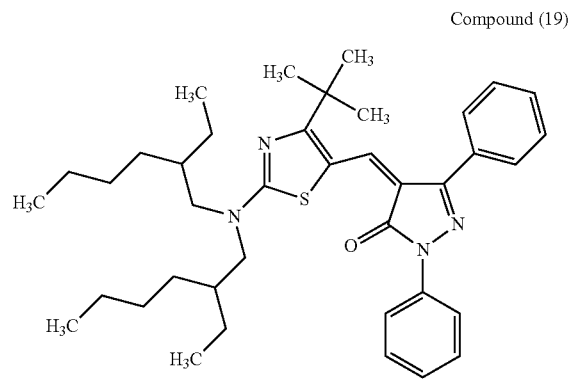
Compound (20)
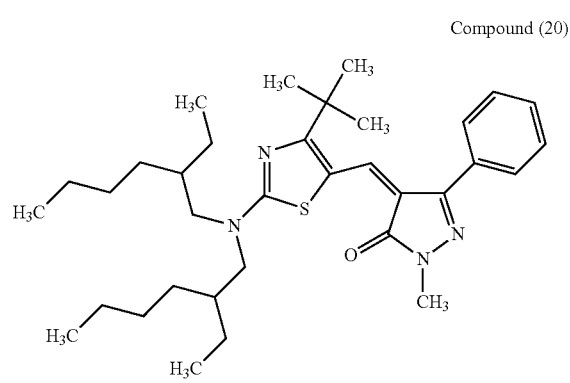
Compound (21)
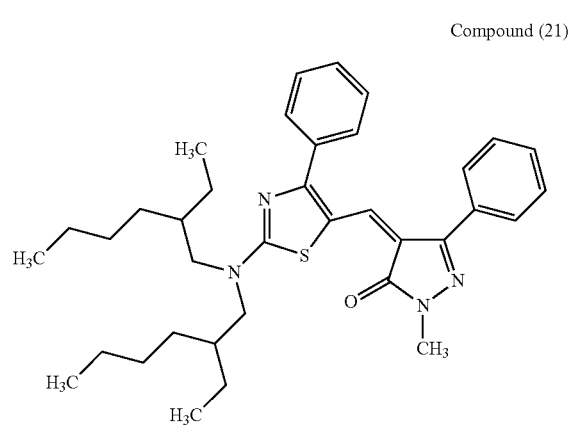
Compound (22)
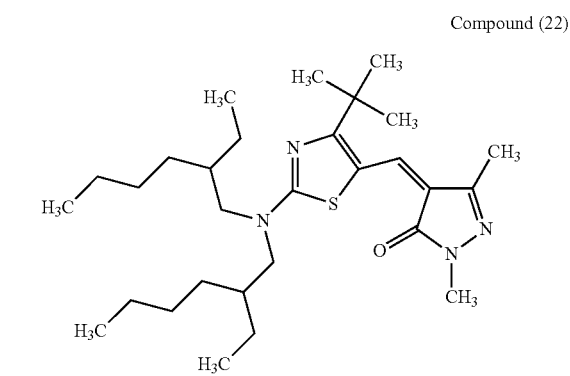
Compound (23)
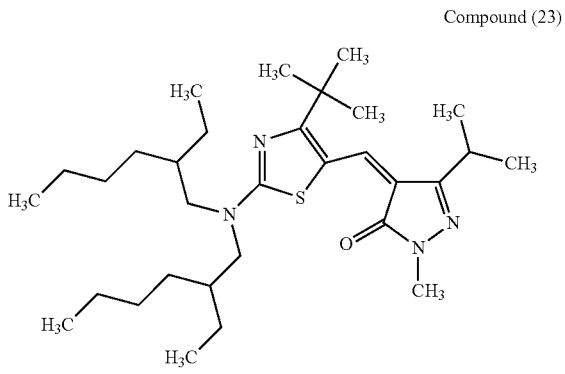
Compound (24)
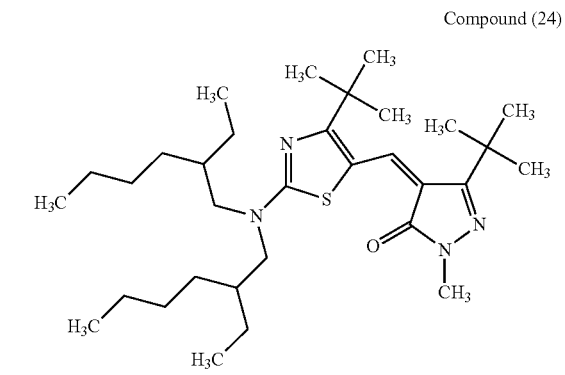
Compound (25)
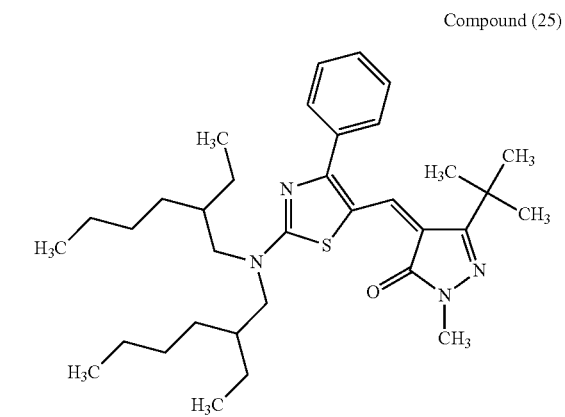
Compound (26)
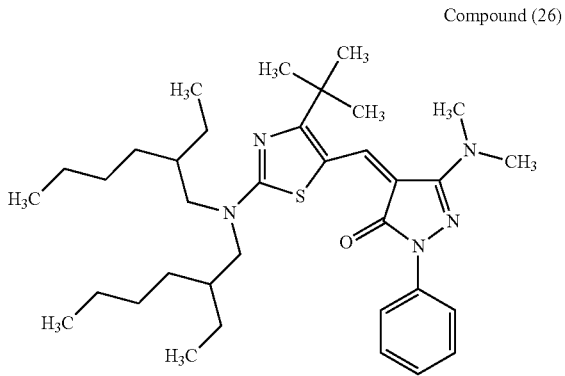

-continued

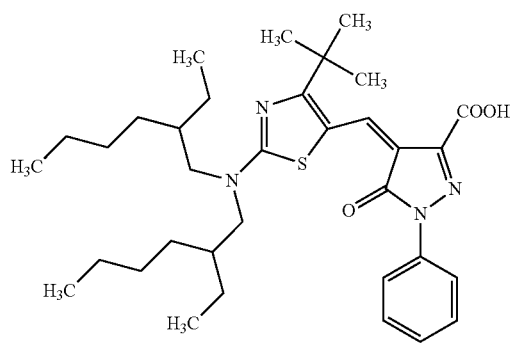

Compound (27)

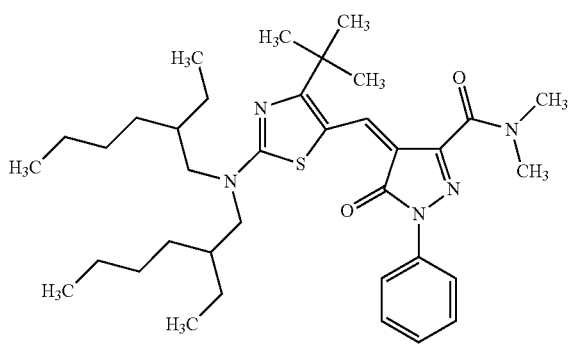

Compound (28)

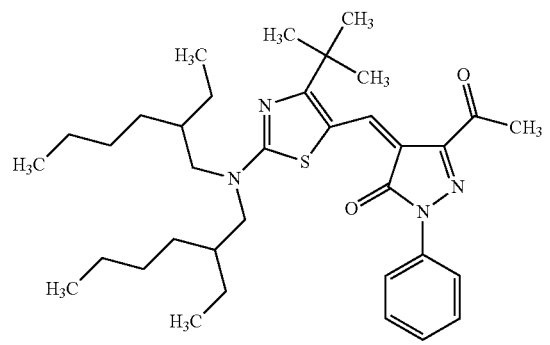

Compound (29)

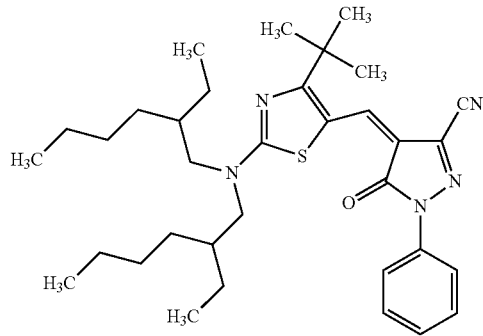

Compound (30)

Ink

The ink of the present disclosure will now be described.

The present compound having the structure expressed by general formula (1) is a lightfast orange color compound and is accordingly suitable as a coloring agent.

The ink of the present disclosure contains a medium and the compound having the structure expressed by general formula (1). Other constituents of the ink are selected depend on the use of the ink, and the ink may contain appropriate additives within a range in which the additives do not affect the characteristic feature of the ink in the intended use.

The ink of the present disclosure is suitable as ink jet ink, printing ink, paint, writing ink, and textile printing ink.

When the ink is used for textile printing, a cloth capable of being dyed with the ink is used. Examples of such a cloth include, but are not limited to, fabrics, knitting, and nonwoven fabrics of a fiber containing polyester, acetate, or triacetate. The cloth may be made of a fiber of cotton, silk, hemp, polyurethane, acrylic resin, nylon, wool, or rayon, or may be a blended fabric of two or more of these fibers.

The thickness of the thread of the cloth may be in the range of 10 d to 100 d, and the thickness of the yarn forming the thread is not limited to, but is desirably 1 d or less.

The ink is also suitably used for forming a color filter resist or as a thermal transfer recording ink or a toner ink.

The ink of the present disclosure may be produced as below.

The present compound is gradually dispersed in a medium with stirring, optionally with other coloring agents, an emulsifier, and a resin. Furthermore, the compound is stably dissolved or more finely dispersed in the medium by applying a mechanical shearing force to the mixture with a dispersing device. Thus the ink is produced.

The term "medium" used herein refers to water or an organic solvent.

If an organic solvent is used as the medium of the ink, the organic solvent can be selected according to the use of the ink and is not particularly limited. More specifically, examples of the organic solvent include alcohols, such as methanol, ethanol, modified ethanol, isopropanol, n-butanol, isobutanol, tert-butanol, sec-butanol, 2-methyl-2-butanol, 3-pentanol, octanol, benzyl alcohol, and cyclohexanol; glycols, such as methyl cellosolve, ethyl cellosolve, diethylene glycol, and diethylene glycol monobutyl ether; ketones, such as acetone, methyl ethyl ketone, and methyl isobutyl ketone; esters, such as ethyl acetate, butyl acetate, ethyl propionate, and cellosolve acetate; aliphatic hydrocarbons, such as hexane, octane, petroleum ether, and cyclohexane; aromatic hydrocarbons such as benzene, toluene, and xylene; halogenated hydrocarbons, such as carbon tetrachloride, trichloroethylene, and tetrabromoethane; ethers, such as diethyl ether, dimethyl glycol, trioxane, and tetrahydrofuran; acetals, such as methylal and diethyl acetal; organic acids, such as formic acid, acetic acid, and propionic acid; and sulfur- or nitrogen-containing organic compound, such as nitrobenzene, dimethylamine, monoethanolamine, pyridine, dimethylsulfoxide, and dimethylformamide.

A polymerizable monomer may be used as the organic solvent of the ink. The polymerizable monomer may be an addition-polymerizable or a condensation-polymerizable monomer. Addition-polymerizable monomers are more suitable. Examples of such a polymerizable monomer include styrene monomers, such as styrene, α-methylstyrene, α-ethylstyrene, o-methylstyrene, m-methylstyrene, p-methylstyrene, o-ethylstyrene, m-ethylstyrene, and p-ethylstyrene; acrylate monomers, such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, and amide acrylate; methacrylate monomers, such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, and amide methacrylate; olefin monomers, such as ethylene, propylene, butylene, butadiene, isoprene, isobutylene, and cyclohexene; vinyl halide monomers, such as vinyl chloride, vinylidene chloride, vinyl bromide, and vinyl iodide; vinyl ester monomers, such as vinyl acetate, vinyl propionate, and vinyl benzoate; vinyl ether monomers, such as vinyl methyl ether, vinyl ethyl ether, and vinyl isobutyl ether; and vinyl ketone monomers, such as vinyl methyl ketone, vinyl hexyl ketone, and methyl isopropenyl ketone. These monomers may be used singly or in combination.

Although the compound having the structure expressed by general formula (1) is used as the coloring agent of the ink, other coloring agents may be used in combination as long as the solubility or dispersibility of the compound is not reduced.

Other coloring agents used in combination with the present compound include, but are not limited to, condensed azo compounds, azo metal complexes, and methine compounds.

The proportion of the coloring agent in the ink may be in the range of 1.0 to 30.0 parts by mass, desirably 2.0 to 20.0 parts by mass, such as 3.0 to 15.0 parts by mass, relative to 100.0 parts by mass of the medium. The coloring agent used with such a proportion can produce a satisfactory tinting strength and can be sufficiently dispersed.

If water is used as the medium in the ink of the present disclosure, an emulsifier may be added, if necessary, so that the coloring agent can be stably dispersed. The emulsifier may be, but is not limited to, a cationic surfactant, an anionic surfactant, or a nonionic surfactant.

Examples of the cationic surfactant include dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactant include fatty acid soaps, such as sodium stearate and sodium dodecanoate; and sodium dodecyl sulfate and sodium dodecylbenzene sulfate.

Examples of the nonionic surfactant include dodecyl polyoxyethylene ether, hexadecyl polyoxyethylene ether, nonylphenyl polyoxyethylene ether, sorbitan monooleate polyoxyethylene ether, and monodecanoyl sucrose.

The ink may further contain a resin. The resin can be selected depending on the use of the ink and is not particularly limited. Examples of the resin include polystyrene resin, styrene copolymer, polyacrylic acid resin, polymethacrylic acid resin, polyacrylate resin, polymethacrylate resin, acrylic copolymer, methacrylic copolymer, polyester resin, polyvinyl ether resin, polyvinyl methyl ether resin, polyvinyl alcohol resin, polyvinyl butyral resin, polyurethane resin, and polypeptide resin. These resins may be used singly or in combination as needed.

The dispersing machine used for dispersing the materials may be, but is not limited to, a rotary shear homogenizer, a media disperser, such as a ball mill, a sand mill, or an attritor, or a high-pressure counter collision dispersing machine.

A known dye may be added to the ink for toning.

Since the ink of the present disclosure contains the compound having the structure expressed by general formula (1), as described above, the ink can exhibit a high light fastness.

Color Filter Resist Composition

The color filter resist composition of the present disclosure will now be described.

The present compound, which is a lightfast orange color compound, can be used for toning of color filter resist compositions.

The color filter resist composition of the present disclosure contains a binding resin, a medium, and the present compound.

The color filter resist composition may be prepared as below. The present compound and a binding resin are added to a medium with stirring. At this time, a polymerizable monomer, a polymerization initiator, and a photo-acid generator may be added, if necessary. Then, the materials are stably dissolved or more finely dispersed by applying a mechanical shearing force thereto with a dispersing device. Thus a color filter resist composition is prepared.

The binding resin used in the color filter resist composition is such that it allows the portions of the resist exposed or shaded for forming pixels to be dissolved in an organic solvent, an alkaline solution, water, or a commercially available developer. From the viewpoint of workability and ease of handling after the formation of the resist, it is advantageous that the binding resin be such that it allows development with water or an alkaline solution.

Such a binding resin may be a copolymer of a hydrophilic polymerizable monomer, such as acrylic acid, methacrylic acid, N-(2-hydroxyethyl)acrylamide, N-vinyl pyrrolidone, or an ammonium salt-containing polymerizable monomer, and a lipophilic polymerizable monomer, such as an acrylic ester, a methacrylic ester, vinyl acetate, styrene, or N-vinyl carbazole, copolymerized by a known process with an appropriate proportion. The binding resin may be used in combination with one or more of a radically polymerizable monomer having an ethylenic unsaturated group, a cationic polymerizable monomer having an oxirane ring or an oxetane ring, a radical generator, an acid generator, and a base generator. The binding resin of this type reduces the solubility of the exposed portion of the resist in the developer when the resist is exposed. Accordingly, the binding resin is used in a negative resist, from which only the shaded portion is removed by development.

Alternatively, a resin having a quinonediazide group capable of being cleaved to produce a carboxy group by being irradiated with light, a binding resin, such as tert-butyl carbonate of a polyhydroxystyrene or tetrahydro pyranyl ether, having a group capable of being cleaved with an acid, and an acid generator capable of generating an acid by exposure may be used in combination. This binding resin increases the solubility of the exposed portion of the resist in the developer, and accordingly can be used in a positive resist, from which only the exposed portion is removed by development.

If the color filter resist composition is a negative resist composition, a polymerizable monomer capable of being addition polymerized by exposure (hereinafter referred to as photopolymerizable monomer) may be advantageously used. The photopolymerizable monomer is desirably a compound having at least one addition polymerizable ethylenic unsaturated double bond and has a boiling point of 100° C. or more at normal pressure. Examples of the photopolymerizable monomer include monofunctional acrylates such as polyethylene glycol monoacrylate, polyethylene glycol monomethacrylate, polypropylene glycol monoacrylate, polypropylene glycol monomethacrylate, phenoxyethyl acrylate, and phenoxyethyl methacrylate; polyfunctional acrylates or methacrylates, such as polyethylene glycol diacrylate, polyethylene glycol dimethacrylate, polypropylene glycol diacrylate, polypropylene glycol dimethacrylate, trimethylolethane triacrylate, trimethylolethane trimethacrylate, trimethylolpropane triacrylate, trimethylolpropane trimethacrylate, trimethylolpropane diacrylate, trimethylolpropane dimethacrylate, neopentyl glycol diacrylate, neopentyl glycol dimethacrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, hexanediol diacrylate, hexanediol dimethacrylate, trimethylolpropane tri(acryloyloxypropyl) ether, tri(acryloyloxyethyl) isocyanurate, tri(acryloyloxyethyl) cyanurate, glycerin triacrylate, and glycerin trimethacrylate; and other polyfunctional acrylates or methacrylates produced by adding ethylene oxide or propylene oxide to a polyfunctional alcohol such as trimethylolpropane or glycerin, and then acrylating or methacrylating the addition reaction product. Other examples include urethane acrylates, polyester acrylates, and polyfunctional epoxy acrylates or epoxy methacrylates produced by a reaction of an epoxy resin with acrylic acid or methacrylic acid. Among these advantageous are trimethylolpropane triacrylate, trimethylolpropane trimethacrylate, pentaerythritol tetraacrylate, pentaerythritol tetramethacrylate, dipentaerythritol hexaacrylate, dipentaerythritol hexamethacrylate, dipentaerythritol pentaacrylate, and dipentaerythritol pentamethacrylate.

The above-cited photopolymerizable monomers may be used singly or in combination.

The content of the photopolymerizable monomer in the resist composition may be 5% to 50% by mass, desirably 10% to 40% by mass, relative to the total mass of the solids of the resist composition. When the photopolymerizable monomer content is 5% to 50% by mass, the sensitivity to exposure increases, and the resist composition has an appropriate adhesion.

If the color filter resist composition is a negative resist composition, the negative resist composition may contain a photopolymerization initiator. Examples of the photopolymerization initiator include vicinal polyketaldonyl compounds, α-carbonyl compounds, acyloin ether, quinone compounds, a combination of triallyl imidazole dimer and p-aminophenyl ketone, and trioxadiazole compounds. Among these advantageous is 2-benzyl-2-dimethylamino-1-(4-morpholinophenyl)butanone (product name: Irgacure 369, produced by BASF). If an electron beam is used for forming pixels with a colored resist using the resist composition of the present disclosure, the resist composition need not contain a photopolymerization initiator.

If the color filter resist composition is a positive resist composition, a photo-acid generator may be added to the resist composition, if necessary. The photo-acid generator may be a salt of an anion and an onium, such as sulfonium, iodonium, selenium, ammonium, or phosphonium, or any other known photo-acid generator.

Sulfonium ions include triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, and phenacyltetrahydrothiophenium.

Exemplary iodonium ions include diphenyliodonium, di-p-tolyliodonium, bis(4-dodecylphenyl)iodonium, bis(4-methoxyphenyl)iodonium, and (4-octyloxyphenyl)phenyliodonium.

Exemplary selenium ions include triaryl seleniums, such as triphenylselenium, tri-p-tolylselenium, tri-o-tolylselenium, tris(4-methoxyphenyl) selenium, 1-naphthyldiphenylselenium, tris(4-fluorophenyl)selenium, tri-1-naphthyl selenium, and tri-2-naphthylselenium.

Exemplary ammonium ions include tetraalkylammonium ions, such as tetramethylammonium, ethyltrimethylammonium, diethyldimethylammonium, triethylmethylammonium, tetraethylammonium, trimethyl-n-propylammonium, trimethylisopropylammonium, trimethyl-n-butylammonium, and trimethylisobutylammonium.

Exemplary phosphonium ions include tetraphenylphosphonium, tetra-p-tolylphosphonium, tetrakis(2-methoxyphenyl)phosphonium, triphenylbenzylphosphonium, triphenylphenacylphosphonium, triphenylmethylphosphonium, triethylbenzylphosphonium, and tetraethylphosphonium.

Examples of the above-mentioned anion include, but are not limited to, halogen acid ions, such as $ClO_4^-$ and $BrO_4^-$; halogenated sulfonic acid ions, such as $FSO_3^-$ and $ClSO_3^-$; sulfate ions, such as $CH_3SO_4^-$, $CF_3SO_4^-$, and $HSO_4^-$; carbonate ions, such as $HCO_3^-$ and $CH_3CO_3^-$; aluminate ions, such as $AlCl_4^-$ and $AlF_4^-$; hexafluorobismuth ion; carboxylate ions, such as $CH_3COO^-$, $CF_3COO^-$, $C_6H_5COO^-$, $CH_3C_6H_4COO^-$, $C_6F_5COO^-$, and $CF_3C_6H_4COO^-$; arylborate ions, such as $B(C_6H_5)_4^-$ and $CH_3CH_2CH_2CH_2B(C_6H_5)_3^-$; thiocyanate ion; and nitrate ion.

The medium used in the color filter resist composition to dissolve or disperse the present compound and the binding resin, and optionally added constituents, such as a photopolymerizable monomer, a photopolymerization initiator, and a photo-acid generator, may be water or an organic solvent. Examples of the organic solvent include cyclohexanone, ethyl cellosolve acetate, butyl cellosolve acetate, 1-methoxy-2-propyl acetate, diethylene glycol dimethyl ether, ethyl benzene, 1,2,4-trichlorobenzene, ethylene glycol diethyl ether, xylene, ethyl cellosolve, methyl n-amyl ketone, propylene glycol monomethyl ether, toluene, methyl ethyl ketone, ethyl acetate, methanol, ethanol, isopropanol, butanol, methyl isobutyl ketone, and petroleum solvents. These solvents may be used singly or in combination. The medium of the color filter resist composition may be the same as or different from the medium used in the above-described ink, as long as it does not reduce the dispersibility of the present compound.

By using the resist composition of the present disclosure for at least one color of a color filter for adjacent pixels of different colors (such as red, green, and blue) having different spectral characteristics, the color filter can be superior in light fastness. In order to ensure desired spectral characteristics, an additional dye may be used for toning. Example of the dye used in combination with the present compound include condensed azo compounds, azo metal complexes, diketopyrrolopyrrole compounds, anthraquinone compounds, quinacridone compounds, naphthol compounds, benzimidazolone compounds, thioindigo compounds, perylene compounds, methine compounds, allylamide compounds, and basic dye lakes. Furthermore, the color filter resist composition of the present disclosure may optionally contain an UV absorbent, or a silane coupling agent for increasing the adhesion with the glass substrate when the filter is formed.

The dispersing machine used for dispersing the materials may be, but is not limited to, a rotary shear homogenizer, a media disperser, such as a ball mill, a sand mill, or an attritor, or a high-pressure counter collision dispersing machine.

Since the color filter resist composition of the present disclosure contains the present lightfast compound, as described above, the color filter resist composition can exhibit a high light fastness.

Thermal Transfer Recording Sheet

The thermal transfer of the present disclosure will now be described.

The present compound, which is a lightfast orange color compound, can be suitably used in a thermal transfer recording sheet.

The thermal transfer recording sheet includes coloring material layers including a yellow layer, a magenta layer, and a cyan layer. For forming an image, the thermal transfer recording sheet is disposed over a coloring material-receiving layer of an image-receiving sheet and heated with a heating device such as a thermal head, so that the coloring materials are transferred from the sheet to the image-receiving sheet.

The thermal transfer recording sheet may be produced by, but not limited to, the following process.

A coloring material containing the compound having the structure expressed by general formula (1) and a binding resin, and optionally a surfactant and a wax, are gradually added to a medium and sufficiently harmonized. Furthermore, the materials are stably dissolved or more finely dispersed by applying a mechanical shearing force to the mixture with a dispersing machine. Thus a dispersion liquid (ink) is prepared. The dispersion liquid is applied to a base film, or substrate, and dried to form a coloring material layer.

In addition, a transferable protective layer and a heat-resistant lubricative layer may be formed, if necessary, and thus, a thermal transfer recording sheet is produced. The method for producing the thermal transfer recording sheet of the present disclosure is not limited to this process.

The constituents of the coloring material layer will now be described in detail.

Coloring Material

A coloring material conventionally used for thermal transfer may be used in combination with the compound having the structure expressed by general formula (1). The coloring material is selected in view of hue, printing sensitivity, light fastness, storage stability, solubility in a binder, and the like.

The proportion of the present compound in the coloring material layer is 1 part to 50 parts by mass relative to 100 parts by mass of the binding resin in the coloring material layer. When it is 3 parts to 20 parts by mass, the coloring material or coloring agent can be satisfactorily dispersed in the dispersion liquid. If a mixture of two or more coloring materials is used, it is desirable that the proportion of the total mass of the coloring materials be within such a range.

Binding Resin

Various binding resins can be used. Suitable binding resins include water-soluble resins, such as cellulose resins, polyacrylic acid resins, starch resins, and epoxy resins; and resins soluble in organic solvent, such as polyacrylate resins, polymethacrylate resins, polystyrene resins, polycarbonate resins, polyethersulfone resins, polyvinylbutyral resins, ethyl cellulose resins, acetyl cellulose resins, polyester resins, AS resins, and phenoxy resins. These resins may be used singly or in combination.

Surfactant

The thermal transfer recording sheet of the present disclosure may contain a surfactant to impart a sufficient lubricity to the sheet when heated by a thermal head for printing. The surfactant may be a cationic surfactant, an anionic surfactant, or a nonionic surfactant.

Examples of the cationic surfactant include dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactant include fatty acid soaps, such as sodium stearate and sodium dodecanoate; and sodium dodecyl sulfate and sodium dodecylbenzene sulfate.

Examples of the nonionic surfactant include dodecyl polyoxyethylene ether, hexadecyl polyoxyethylene ether, nonylphenyl polyoxyethylene ether, Sorbitan monooleate polyoxyethylene ether, and monodecanoyl sucrose.

Wax

The thermal transfer recording sheet of the present disclosure may contain a wax to impart a sufficient lubricity to the sheet when not heated by a thermal head. The wax to be added to the sheet may be, but is not limited to, a polyethylene wax, a paraffin wax, or a fatty acid ester wax.

The thermal transfer recording sheet may further contain other additives, such as an UV absorbent, a preservative, an antioxidant, an antistatic agent, and a viscosity modifier, if necessary.

Medium

The medium used for preparing the dispersion used for forming the coloring material layer may be water or an organic solvent. Examples of the organic solvent include alcohols, such as methanol, ethanol, isopropanol, and isobutanol; cellosolves, such as methyl cellosolve and ethyl cellosolve; aromatic hydrocarbons, such as toluene, xylene, and chlorobenzene; esters, such as ethyl acetate and butyl acetate; ketones, such as acetone, methyl ethyl ketone, methyl isobutyl ketone, and cyclohexanone; halogenated hydrocarbons, such as methylene chloride, chloroform, and trichloroethylene; ethers, such as tetrahydrofuran and dioxane; and N,N-dimethylformamide and N-methylpyrrolidone. These organic solvents may be used singly or in combination.

The substrate of the thermal transfer recording sheet will now be described.

The substrate, which is intended to support the coloring material layer, may be made of any material without particular limitation, as long as it is a film having a certain heat resistance and strength. Examples of the substrate include polyethylene terephthalate films, polyethylene naphthalate films, polycarbonate films, polyimide films, polyamide films, aramid films, polystyrene films, 1,4-polycyclohexylenedimethylene terephthalate films, polysulfone films, polypropylene films, polyphenylene sulfide films, polyvinyl alcohol films, cellophane, films of cellulose derivatives, polyethylene films, polyvinyl chloride films, nylon films, condenser paper, and paraffin paper. Polyethylene terephthalate films are advantageous in terms of mechanical strength, resistance to solvent, and economical efficiency.

The thickness of the substrate may be 0.5 μm to 50 μm, and is desirably 3 μm to 10 μm in view of easy transfer.

If a dye ink is applied onto the substrate for forming the coloring material layer, the wettability and adhesion of the dye ink tend to be insufficient. In this instance, it is advantageous to apply a treatment for enhancing adhesion to either or both of the surfaces of the substrate, if necessary.

The treatment may be, but is not limited to, ozone treatment, corona discharge treatment, UV radiation treatment, plasma treatment, low-temperature plasma treatment, primer treatment, or chemical treatment. Two or more of these treatments may be combined.

As such treatment, an adhesion layer may be formed on the substrate.

The adhesion layer may be made of, but not limited to, particles of an organic material, such as polyester resin, polystyrene resin, polyacrylic ester resin, polyamide resin, polyether resin, polyvinyl acetate resin, polyethylene resin, polypropylene resin, polyvinyl chloride resin, polyvinyl alcohol resin, or polyvinyl butyral resin, or particles of an inorganic material, such as silica, alumina, magnesium carbonate, magnesium oxide, or titanium oxide.

Toner

The toner of the present disclosure will now be described.

The present compound, which has a high light fastness, can be suitably used in a toner.

Toner particles of the toner of the present disclosure may be produced by pulverization, suspension polymerization, suspension granulation, emulsion polymerization, or emulsion aggregation.

When the compound having the structure expressed by general formula (1) is used as a coloring agent, pulverization is advantageous. The toner of the present disclosure may be used in a developer (hereinafter referred to as liquid developer) used for liquid development.

The present compound may be used singly or in combination with one or more known pigments or dyes for adjusting the color of the toner, depending on the process for producing the toner.

Exemplary Method for Producing Toner

The toner of the present disclosure may optionally contain a magnetic material, a wax, a charge control agent, or any other additive.

The toner may be produced using a mixer, a heat kneader, a classifier, or any other known machine.

First, materials of the toner are sufficiently mixed with a mixer, such as a Henschel mixer or a ball mill. Then, the mixture is melted with a heat kneader such as a roll, a kneader, or an extruder. Furthermore, a wax and a magnetic material are dispersed in the mixture in which the resin materials are dissolved in each other by being kneaded. After cooling and solidification, the product is pulverized and sized to yield a toner.

The toner may contain a binding resin, and examples of the binding resin include vinyl resin, polyester resin, epoxy resin, polyurethane resin, polyvinyl butyral resin, terpene resin, phenol resin, aliphatic or alicyclic hydrocarbon-based resin, aromatic petroleum-based resin, rosin, and modified rosin. Vinyl resin and polyester resin are advantageous in view of chargeability and fixability. In particular, polyester resin is highly effective in increasing chargeability and fixability and is thus more advantageous.

Those binding resins may be used singly or in combination. If two or more binding resins are used in combination, it is desirable to use resins having different molecular to control the viscoelasticity of the toner.

The binding resin desirably has a glass transition temperature of 45° C. to 80° C., more desirably 55° C. to 70° C., a number-average molecular weight (Mn) of 1,500 to 50,000, and a weight average molecular weight (Mw) of 6,000 to 1,000,000.

If a polyester resin is used as the binding resin, the alcohol component/acid component proportion in the polyester resin is 45/55 to 55/45 on a mole basis.

As the number of the terminal groups of the polyester resin is increased, the chargeability of the toner becomes more dependent on environment. Accordingly, the acid value of the polyester resin is desirably 90 mg KOH/g or less, and more desirably 50 mg KOH/g or less. Also, the hydroxy value of the polyester resin is desirably 50 mg KOH/g or less, and more desirably 30 mg KOH/g or less.

Method for Preparing Liquid Developer

A method for preparing a liquid developer containing the toner of the present disclosure will now be described.

The liquid developer may be prepared by dispersing or dissolving a coloring resin powder, which acts as the toner, and optionally additives such as a charge control agent and a wax, in an electrically insulating carrier liquid. Alternatively, the liquid developer may be prepared by a two-step process in such a manner that a previously prepared concentrated toner liquid is diluted with an electrically insulating carrier liquid.

For dispersing the toner, a dispersing machine is used, and examples thereof include, but are not limited to, rotary shear homogenizers, media dispersing devices such as a ball mill, a sand mill, and an attritor, and high-pressure counter collision dispersing machines.

The liquid developer may further contain two or more pigment or dye as a coloring agent in addition to the toner as a coloring resin powder.

The wax and the coloring agent can be selected from those that have been described herein.

The charge control agent used in the liquid developer may be selected from those used in liquid developers for electrostatic development without particular limitation, and examples of such a charge control agent include cobalt naphthenate, copper naphthenate, copper oleate, cobalt oleate, zirconium octylate, cobalt octylate, sodium dodecylbenzenesulfonate, calcium dodecylbenzenesulfonate, soybean lecithin, and aluminum octoate.

The electrically insulating carrier liquid may be, but is not limited to, an organic solvent having a high electric resistance of $10^9$ Ω·cm or more and a low dielectric constant of 3 or less.

Examples of the electrically insulating carrier liquid include aliphatic hydrocarbons, such as hexane, pentane, octane, nonane, decane, undecane, and dodecane; and commercially available products having a boiling point in the range of 68° C. to 250° C., such as ISOPAR series H, G, K, L, and M (each produced by Exxon Mobil) and Linealene Dimers A-20 and A-20H (each produced by Idemitsu Kosan). These carrier liquids may be used singly or in combination as long as the viscosity of the liquid developer is not increased.

EXAMPLES

The subject matter of the present disclosure will be further described in detail with reference to the following Examples. It is however not limited to the disclosed Examples. In the following description, "part(s)" and "%" are on a mass basis unless otherwise specified. The compounds produced for the following Examples were identified using a proton nuclear magnetic resonance spectroscopy ($^1$H-NMR) analyzer (ECA-400, manufactured by JEOL) and a liquid chromatography/time-of-flight mass spectrometry (LC/TOF MS) analyzer (LC/MSD TOF, manufactured by Agilent Technologies).

Production of Compound Having Structure Expressed by General Formula (1)

The compound having the structure expressed by general formula (1) can be synthesized by a known process.

Compounds having a structure expressed by general formula (1) were synthesized by the following processes.

Process Example 1

Production of Compound (1)

To 25 mL of suspension of 12 mmol of ethyl acetoacetate in ethanol, 12 mmol of phenylhydrazine was added. The resulting liquid was heated to 80° C. and refluxed for 3 hours. Then, 11 mmol of aldehyde (1) and 13 mmol of ammonium acetate were added, and the mixture was heated to 80° C. and refluxed for 3 hours. After the completion of the reaction, the reaction product was cooled to room temperature and concentrated under reduced pressure. To the reaction product were added 50 mL of ethyl acetate and 50 mL of water. After the mixture was neutralized with saturated sodium hydrogencarbonate solution, the reaction product was separated. The organic phase was concentrated under reduced pressure. Then, the residue was purified by column chromatography (eluent: ethyl acetate/hexane) to yield compound (1) (yield: 19.3%).

Identification Results of Compound (1)
[1] $^1$H-NMR (400 MHz, CDCl$_3$, room temperature): δ (ppm)=0.97 (6H, dd, J=5.3, 12.6 Hz), 0.94-0.99 (4H, m), 1.53 (9H, s), 1.64-1.71 (4H, m), 2.28 (3H, s), 3.56 (4H, br), 7.12 (1H, t, J=7.3 Hz), 7.38 (2H, dd, J=5.3, 10.8 Hz), 7.98 (3H, dd, J=8.7, 9.6 Hz)
[2] Mass spectrometry (ESI-TOF): m/z=453.2820 (M+H)$^+$ Process Example 2

Production of Compound (3)

The following compound was produced in the same manner as in Process Example 1, and the resulting compound was identified.

Identification Results of Compound (3)
[1] $^1$H-NMR (400 MHz, CDCl$_3$, room temperature): δ (ppm)=0.90 (12H, t, J=7.1 Hz), 1.19-1.40 (16H, m), 1.55 (9H, s), 1.87 (2H, t, J=5.6 Hz), 2.28 (3H, s), 3.38 (2H, br), 3.62 (2H, br), 7.12 (1H, t, J=7.33 Hz), 7.37 (2H, t, J=7.79 Hz), 7.97 (3H, dd, J=4.8, 5.7 Hz)
[2] Mass spectrometry (ESI-TOF): m/z=565.4030 (M+H)$^+$ Process Example 3

Production of Compound (6)

Identification Results of Compound (6)
[1] $^1$H-NMR (400 MHz, DMSO, room temperature): δ (ppm)=0.87 (12H, d, J=6.9 Hz), 1.14-1.39 (16H, m), 1.49 (9H, s), 1.90 (2H, br), 2.09 (2H, s), 2.23 (3H, s), 2.29 (3H, s), 3.68 (2H, br), 7.18 (2H, d, J=8.2 Hz), 7.80 (2H, d, J=8.7 Hz), 7.92 (1H, s)
[2] Mass spectrometry (ESI-TOF): m/z=579.4104 (M+H)$^+$ Process Example 4

Production of Compound (7)

Identification Results of Compound (7)
[1] $^1$H-NMR (400 MHz, DMSO, room temperature): δ (ppm)=0.88 (12H, t, J=6.9 Hz), 1.14-1.39 (16H, m), 1.49 (9H, s), 1.90 (2H, br), 2.09 (2H, s), 2.23 (3H, s), 3.68 (2H, br), 3.76 (3H, s), 6.95 (2H, dd, J=2.1, 7.1 Hz), 7.79 (2H, dd, J=1.8, 6.9 Hz), 7.92 (1H, s)
[2] Mass spectrometry (ESI-TOF): m/z=595.4071 (M+H)$^+$ Process Example 5

Production of Compound (9)

Identification Results of Compound (9)
[1] $^1$H-NMR (400 MHz, CDCl$_3$, room temperature): δ (ppm)=0.91 (12H, dd, J=6.9, 14.7 Hz), 1.20-1.40 (16H, m), 1.91 (2H, s), 2.13 (3H, s), 3.49 (2H, br), 3.69 (2H, br), 7.13 (1H, t, J=7.3 Hz), 7.38 (2H, t, J=8.01 Hz), 7.51 (4H, t, J=2.8 Hz), 7.66 (2H, dd, J=3.0, 6.6 Hz), 7.97 (2H, d, J=7.8 Hz)
[2] Mass spectrometry (ESI-TOF): m/z=585.3659 (M+H)$^+$ Process Example 6

Production of Compound (11)

Identification Results of Compound (11)
[1] $^1$H-NMR (400 MHz, CDCl$_3$, room temperature): δ (ppm)=0.90 (12H, br), 1.20-1.40 (16H, m), 1.53 (9H, s), 1.80-1.98 (2H, m), 2.28 (3H, s), 3.36 (2H, br), 3.65 (2H, br), 4.95 (2H, br), 7.48 (1H, t, J=8.0 Hz), 7.64 (1H, d, J=8.2 Hz), 8.0 (1H, s), 8.28 (1H, d, J=8.2 Hz), 8.61 (1H, s)
[2] Mass spectrometry (ESI-TOF): m/z=644.3670 (M+H)$^+$ Process Example 7

Production of Compound (13)

Identification Results of Compound (13)
[1] $^1$H-NMR (400 MHz, DMSO, room temperature): δ (ppm)=0.87 (15H, d, J=6.4 Hz), 1.18-1.39 (18H, m), 1.49 (9H, s), 1.91 (2H, br), 2.09 (2H, s), 2.65 (2H, q, J=7.5 Hz), 3.68 (2H, br), 7.13 (1H, t, J=7.3 Hz), 7.39 (2H, t, J=7.8 Hz), 7.94 (3H, t, J=6.2 Hz)
[2] Mass spectrometry (ESI-TOF): m/z=579.4096 (M+H)$^+$ Process Example 8

Production of Compound (14)

Identification Results of Compound (14)
[1] $^1$H-NMR (400 MHz, DMSO, room temperature): δ (ppm)=0.88 (12H, br), 1.19-1.41 (16H, m), 1.40 (9H, s), 1.50 (9H, s), 2.09 (2H, s), 2.30 (3H, s), 7.20 (2H, d, J=8.2 Hz), 7.81 (2H, d, J=8.7 Hz), 8.27 (1H, s)
[2] Mass spectrometry (ESI-TOF): m/z=621.4564 (M+H)$^+$ Process Example 9

Production of Compound (15)

Identification Results of Compound (15)
[1] $^1$H-NMR (400M Hz, DMSO, room temperature): δ (ppm)=0.88 (12H, br), 1.19-1.37 (18H, m), 1.42 (9H, s), 1.51 (9H, s), 1.91 (2H, br), 3.66 (2H, br), 7.14 (1H, t, J=7.3 Hz), 7.39 (2H, t, J=8.0 Hz), 7.94 (2H, d, J=7.8 Hz), 8.29 (1H, s)
[2] Mass spectrometry (ESI-TOF): m/z=607.4399 (M+H)$^+$ Process Example 9

Production of Compound (16)

Identification Results of Compound (16)
[1] $^1$H-NMR (400 MHz, CDCl$_3$, room temperature): δ (ppm)=0.90 (12H, br), 1.20-1.46 (16H, m), 1.44 (3H, t, J=7.1 Hz), 1.57 (9H, s), 1.88 (2H, br), 3.36 (2H, br), 3.71 (2H, br), 4.46 (2H, q, J=7.2 Hz), 7.20 (1H, t, J=7.3 Hz), 7.40 (2H, dd, J=5.0, 10.5 Hz), 7.96 (2H, dd, J=1.1, 8.5 Hz)
[2] Mass spectrometry (ESI-TOF): m/z=623.4050 (M+H)$^+$ Process Example 10

Production of Compound (19)

Identification Results of Compound (19)
[1] $^1$H-NMR (400 MHz, DMSO, room temperature): δ (ppm)=0.87-0.83 (12H, m), 1.20-1.39 (16H, m), 1.48 (9H, s), 1.99 (2H, br), 2.09 (2H, s), 3.68 (2H, br), 7.18 (1H, t, J=7.3 Hz), 7.43 (2H, t, J=8.0 Hz), 7.54-7.59 (3H, m), 7.65 (2H, dd, J=1.8, 7.8 Hz), 8.01 (2H, d, J=7.8 Hz), 8.09 (1H, s)
[2] Mass spectrometry (ESI-TOF): m/z=627.4125 (M+H)$^+$ Process Example 11

Production of Compound (20)

Identification Results of Compound (20)
[1] $^1$H-NMR (400 MHz, CDCl$_3$, room temperature): δ (ppm)=0.89 (12H, d, J=5.5 Hz), 1.20-1.40 (25H, m), 1.87 (2H, br), 2.17 (2H, s), 3.49 (2H, br), 3.51 (3H, s), 7.42-7.48 (3H, m), 7.55 (2H, dd, J=1.6, 8.0 Hz), 8.11 (1H, s)
[2] Mass spectrometry (ESI-TOF): m/z=565.3957 (M+H)$^+$ Process Example 12

Production of Compound (22)

Identification Results of Compound (22)
[1] $^1$H-NMR (400 MHz, CDCl$_3$, room temperature): δ (ppm)=0.90 (12H, t, J=6.9 Hz), 1.20-1.40 (16H, m), 1.87 (2H, br), 2.18 (3H, s), 3.36 (5H, br), 3.51 (2H, br), 7.92 (1H, s)
[2] Mass spectrometry (ESI-TOF): m/z=503.3890 (M+H)$^+$ Process Example 13

Production of Compound (23)

Identification Results of Compound (23)
[1] $^1$H-NMR (400 MHz, DMSO, room temperature): δ (ppm)=0.87 (12H, t, J=7.6 Hz), 1.20-1.39 (24H, m), 1.46 (9H, s), 1.89 (2H, br), 2.09 (2H, s), 2.92 (1H, t, J=6.9 Hz), 3.20 (3H, s), 7.88 (1H, s)
[2] Mass spectrometry (ESI-TOF): m/z=531.4114 (M+H)$^+$ Process Example 14

Production of Compound (24)

Identification Results of Compound (24)
[1] $^1$H-NMR (400 MHz, DMSO, room temperature): δ (ppm)=0.87 (12H, t, J=7.3 Hz), 1.14-1.39 (25H, m), 1.47 (9H, s), 1.89 (2H, br), 2.09 (2H, s), 3.20 (3H, s), 3.60 (2H, br), 8.17 (1H, s)
[2] Mass spectrometry (ESI-TOF): m/z=545.4267 (M+H)$^+$ Preparation of Inks Inks according to the present disclosure and inks for comparison were prepared in the following procedure.

Preparation of Ink (1)

Ink (1) according to the present disclosure was prepared by mixing 5 parts of compound (1), which is a present compound, 350 parts of toluene, 350 parts of ethyl acetate, and 300 parts of 2-butanone.

Preparation of Inks (2) to (15)

Inks (2) to (15) were prepared in the same manner as ink (1) except that compound (1) was replaced with the compound shown in Table 1.

Preparation of Comparative Inks (1) and (2)

Comparative inks (1) and (2) were prepared in the same manner as ink (1) except that compound (1) was replaced with the following comparative compounds (1) and (2), respectively.

Comparative Compound (1)

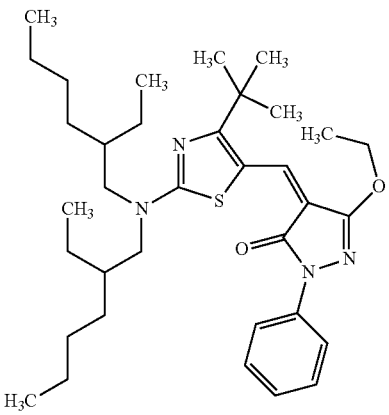

Comparative Compound (2)

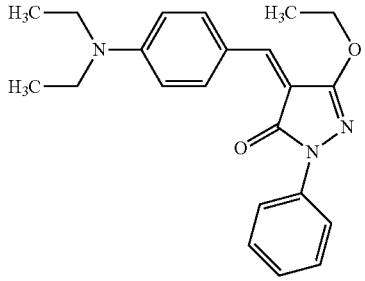

Evaluations

Preparation of Samples

Each of inks (1) to (15) and comparative inks (1) and (2) was applied to coverage measurement test paper by bar coating (Bar No. 10) and then allowed to stand overnight for drying. Thus, image samples were prepared. For each of the resulting image samples, the color parameters (L*, a*, and b*) in the CIE L*a*b* color system were measured with a reflection densitometer SpectroLino (manufactured by Gretag Macbeth).

Rating of Ink Chromaticity

The chromaticity of each ink was estimated as below.

Color deviation α defined as below was calculated using chromaticity parameters a* and b* at L=60.

$$\alpha=|b^*/a^*-1.5|$$

A: α was less than 0.20 (close to orange color).
B: α was in the range of 0.20 to less than 0.50 (rather close to orange color).
C: α was 0.50 or more (different from orange color).

Rating of Ink Light Fastness

Each image sample was exposed to an environment of an illuminance of 340 nm at 0.39 W/m$^2$ and at a temperature of 40° C. and a relative humidity of 60% for 5 hours in a xenon test apparatus Atlas Ci 4000 (manufactured by Suga Test Instruments). The reflected density of the printed image was measured before and after the exposure test. The color difference ΔE was defined as below using initial color parameters $a_0^*$, $b_0^*$, and $L_0^*$ and color parameters $a^*$, $b^*$, and $L^*$ after exposure:

$$\Delta E = \sqrt{(a^*-a_0^*)^2+(b^*-b_0^*)^2+(L^*-L_0^*)^2}$$

The rating criteria were as follows.
A: ΔE<4.00 (excellent light fastness)
B: 4.00≤ΔE<8.0 (good light fastness)
C: 8.0≤ΔE (poor light fastness)

Table 1 shows the evaluation results of Examples and Comparative Examples.

TABLE 1

|  | Ink | Compound used | a* | b* | α | Rating | ΔE after 5 h | Light fastness rating |
|---|---|---|---|---|---|---|---|---|
| Example 1 | Ink (1) | Compound (1) | 60.0 | 102 | 0.21 | B | 2.48 | A |
| Example 2 | Ink (2) | Compound (3) | 59.2 | 105 | 0.27 | B | 3.54 | A |
| Example 3 | Ink (3) | Compound (6) | 59.6 | 103 | 0.23 | B | 3.12 | A |
| Example 4 | Ink (4) | Compound (7) | 62.0 | 97.6 | 0.07 | A | 2.75 | A |
| Example 5 | Ink (5) | Compound (9) | 58.8 | 83.2 | 0.09 | A | 3.42 | A |
| Example 6 | Ink (6) | Compound (11) | 61.6 | 103 | 0.18 | A | 4.86 | B |
| Example 7 | Ink (7) | Compound (14) | 59.7 | 106 | 0.28 | B | 4.80 | B |
| Example 8 | Ink (8) | Compound (16) | 65.0 | 72.0 | 0.39 | B | 4.90 | B |
| Example 9 | Ink (9) | Compound (19) | 65.2 | 94.6 | 0.05 | A | 3.60 | A |
| Example 10 | Ink (10) | Compound (20) | 66.9 | 95.4 | 0.07 | A | 2.80 | A |
| Example 11 | Ink (11) | Compound (22) | 58.5 | 102 | 0.24 | B | 2.40 | B |
| Example 12 | Ink (12) | Compound (13) | 64.8 | 99.6 | 0.04 | A | 2.35 | A |
| Example 13 | Ink (13) | Compound (15) | 62.9 | 102 | 0.12 | A | 2.90 | A |
| Example 14 | Ink (14) | Compound (23) | 64.7 | 100 | 0.05 | A | 3.60 | A |
| Example 15 | Ink (15) | Compound (24) | 65.0 | 101 | 0.05 | A | 3.10 | A |
| Comparative Example 1 | Comparative ink (1) | Comparative Compound (1) | 51.9 | 110 | 0.62 | C | 4.33 | B |
| Comparative Example 2 | Comparative ink (2) | Comparative Compound (2) | 66.8 | 63.6 | 0.55 | C | 9.00 | C |

As clearly shown in Table 1, the present compounds having the structure expressed by general formula (1) are each a lightfast orange color compound having a higher light fastness than the comparative compounds.

Preparation of Color Filter Resist Composition

Example 16

Resist composition ink (1) used in a resist composition according to the present disclosure was prepared by mixing 12 parts of compound (1) and 120 parts of cyclohexanone, and dispersing the constituents with an attritor (manufactured by Nippon Coke & Engineering) for 1 hour.

To a solution containing 6.7 parts of acrylic copolymer (weight average molecular weight Mw: 10,000) composition containing monomers of 40% by mass of n-butyl methacrylate, 30% by mass of acrylic acid, and 30% by mass of hydroxymethyl methacrylate, 1.3 parts of dipentaerythritol pentaacrylate, and 0.4 part of 2-benzyl-2-dimethylamino-1-(4-morpholinophenyl)-butanone (photopolymerization initiator) in 96 parts of cyclohexanone, 22 parts of the above-prepared resist composition ink (1) was gradually added. The mixture was stirred at room temperature for 3 hours. Then, the mixture was passed through a 1.5 μm filter to yield color filter resist composition (1).

Color filter resist composition (1) was applied onto a glass substrate by spin coating. After being dried at 90° C. for 3 minutes, the coating was exposed to light over the entire surface and subjected to post curing at 180° C., thus forming color filter (1).

Examples 17 to 21

Color filter resist compositions (2) to (6) were prepared in the same manner as in Example 16, except that compound (1) was replaced with the compound shown in Table 2. Then, color filters (2) to (6) were formed in the same manner as in Example 16, except that color filter resist composition (1) was replaced with color filter resist compositions (2) to (6), respectively.

Comparative Examples 3 and 4

Comparative color filter resist compositions (1) and (2) were prepared in the same manner as in Example 16, except that compound (1) was replaced with comparative compounds (1) and (2), respectively. Then, comparative color filters (1) and (2) were formed in the same manner as in Example 16, except that color filter resist composition (1) was replaced with comparative color filter resist compositions (1) and (2), respectively.

Rating of Color Filter Chromaticity

The chromaticity of each color filter was estimated as below.

Color deviation a defined as below was calculated using chromaticity parameters $a^*$ and $b^*$ at $L^*=60$.

$$\alpha = |b^*/a^* - 1.5|$$

A: α was less than 0.20 (close to orange color).
B: α was in the range of 0.20 to less than 0.50 (rather close to orange color).
C: α was 0.50 or more (different from orange color).

Rating of Color Filter Light Fastness

Each color filter was exposed to an environment of an illuminance of 340 nm at 0.39 W/m² and at a temperature of 40° C. and a relative humidity of 60% for 5 hours in a xenon test apparatus Atlas Ci 4000 (manufactured by Suga Test Instruments). The chromaticity of each color filter was measured before and after the exposure test. The color difference ΔE was defined as below using initial color parameters $a_0^*$, $b_0^*$, and $L_0^*$ and color parameters $a^*$, $b^*$, and $L^*$ after exposure:

$$\Delta E = \sqrt{(a^*-a_0^*)^2+(b^*-b_0^*)^2+(L^*-L_0^*)^2}$$

The rating criteria were as follows.
A: ΔE<4.00 (excellent light fastness)
B: 4.00≤ΔE<8.0 (good light fastness)
C: 8.0ΔE (poor light fastness)

Table 2 shows the evaluation results of Examples and Comparative Examples.

TABLE 2

| | Compound used | Use | a* | b* | α | Rating | ΔE after 5 h | Light fastness rating |
|---|---|---|---|---|---|---|---|---|
| Example 16 | Compound (1) | Color filter (1) | 61.2 | 103 | 0.18 | A | 2.51 | A |
| Example 17 | Compound (3) | Color filter (2) | 59.5 | 104 | 0.25 | B | 3.34 | A |
| Example 18 | Compound (6) | Color filter (3) | 58.3 | 102 | 0.25 | B | 3.10 | A |
| Example 19 | Compound (7) | Color filter (4) | 61.9 | 97.8 | 0.08 | A | 2.84 | A |
| Example 20 | Compound (13) | Color filter (5) | 65.3 | 100 | 0.03 | A | 2.50 | A |
| Example 21 | Compound (23) | Color filter (6) | 65.2 | 101 | 0.05 | A | 3.75 | A |
| Comparative Example 3 | Comparative Compound (1) | Comparative color filter (1) | 51.4 | 109 | 0.62 | C | 4.21 | B |
| Comparative Example 4 | Comparative Compound (2) | Comparative color filter (2) | 66.6 | 64.2 | 0.54 | C | 9.05 | C |

Table 2 suggests that the color filters containing a compound according to the present disclosure having the structure expressed by general formula (1) have a more lightfast orange color than the color filters containing a comparative compound.

Production of Thermal Transfer Recording Sheets

Example 22

To a mixed solution of 13.5 parts of compound (1), which is a compound according to the present disclosure, and a mixed solvent of 45 parts of methyl ethyl ketone and 45 parts of toluene, 5 parts of polyvinyl butyral resin Denka 3000-K (produced by Denki Kagaku Kogyo) was gradually added to yield thermal transfer recording sheet ink (1) for forming a thermal transfer recording sheet according to the present disclosure.

The resulting thermal transfer recording sheet ink (1) was applied onto a 4.5 μm-thick polyethylene terephthalate film Lumirror (manufactured by Toray) so that the thickness after drying would be 1 μm, and was then dried to yield thermal transfer recording sheet (1).

Examples 23 to 31

Thermal transfer recording sheets (2) to (10) were produced in the same manner as in Example 22, except that compound (1), which is a compound according to the present disclosure, was replaced with the compound shown in Table 3.

Comparative Examples 5 and 6

Comparative thermal transfer recording sheets (1) and (2) were produced in the same manner as in Example 22, except that compound (1) was replaced with comparative compounds (1) and (2), respectively.

Evaluations
Preparation of Samples

Image samples were prepared by transferring the compound from each of thermal transfer recording sheets (1) to (10) and comparative thermal transfer recording sheets (1) and (2) to printing paper with a modified Canon Selphy.

Rating of Thermal Transfer Recording Sheet Chromaticity

The chromaticity of each sample was estimated as below.

Color deviation α defined as below was calculated using chromaticity parameters a* and b* at L*=60.

$$\alpha=|b^*/a^*-1.5|$$

A: α was less than 0.20 (close to orange color).
B: α was in the range of 0.20 to less than 0.50 (rather close to orange color).
C: α was 0.50 or more (different from orange color).

Rating of Thermal Transfer Recording Sheet Light Fastness

Each image sample was exposed to an environment of an illuminance of 340 nm at 0.39 W/m² and at a temperature of 40° C. and a relative humidity of 60% for 5 hours in a xenon test apparatus Atlas Ci 4000 (manufactured by Suga Test Instruments). The reflected density of the printed image was measured before and after the exposure test. The color difference ΔE was defined as below using initial color parameters $a_0^*$, $b_0^*$, and $L_{=0}^*$ and color parameters a*, b*, and L* after exposure:

$$\Delta E=\sqrt{(a^*-a_0^*)^2+(b^*-b_0^*)^2+(L^*-L_0^*)^2}$$

The rating criteria were as follows.
A: ΔE<4.00 (excellent light fastness)
B: 4.00≤ΔE<8.0 (good light fastness)
C: 8.0≤ΔE (poor light fastness)

Table 3 shows the evaluation results of Examples and Comparative Examples.

TABLE 3

| | Compound used | Use | a* | b* | α | Rating | ΔE after 5 h | Light fastness rating |
|---|---|---|---|---|---|---|---|---|
| Example 22 | Compound (1) | Thermal transfer sheet (1) | 59.8 | 102 | 0.21 | B | 2.32 | A |
| Example 23 | Compound (3) | Thermal transfer sheet (2) | 59.1 | 106 | 0.29 | B | 3.31 | A |
| Example 24 | Compound (6) | Thermal transfer sheet (3) | 61.1 | 103 | 0.19 | A | 3.01 | A |
| Example 25 | Compound (11) | Thermal transfer sheet (4) | 61.6 | 103 | 0.18 | A | 4.55 | B |

TABLE 3-continued

| Compound used | Use | a* | b* | α | Rating | ΔE after 5 h | Light fastness rating |
|---|---|---|---|---|---|---|---|
| Example 26 | Compound (14) | Thermal transfer sheet (5) | 59.9 | 106 | 0.27 | B | 4.80 | B |
| Example 27 | Compound (20) | Thermal transfer sheet (6) | 67.1 | 95.4 | 0.08 | A | 2.62 | A |
| Example 28 | Compound (13) | Thermal transfer sheet (7) | 63.9 | 99.0 | 0.05 | A | 2.40 | A |
| Example 29 | Compound (15) | Thermal transfer sheet (8) | 62.2 | 101 | 0.12 | A | 2.85 | A |
| Example 30 | Compound (23) | Thermal transfer sheet (9) | 64.1 | 99.8 | 0.06 | A | 3.02 | A |
| Example 31 | Compound (24) | Thermal transfer sheet (10) | 64.2 | 100 | 0.06 | A | 3.00 | A |
| Comparative Example 5 | Comparative Compound (1) | Comparative thermal transfer sheet (1) | 52.0 | 109 | 0.60 | C | 4.31 | B |
| Comparative Example 6 | Comparative Compound (2) | Comparative thermal transfer sheet (2) | 69.1 | 64.1 | 0.57 | C | 8.85 | C |

As clearly shown in Table 3, the thermal transfer recording sheets using a compound having the structure expressed by general formula (1) have a more lightfast orange color than the comparative thermal transfer recording sheets using comparative compounds.

Production of Toners

Example 32

Binding resin (polyester resin): 100 parts by mass
(Tg: 55° C., acid value: 20 mg KOH/g, hydroxy value: 16 mg KOH/g, molecular weights Mp (peak molecular weight): 4500, Mn: 2300, Mw: 38000)
Compound (1): 5 parts by mass
Aluminum 1,4-di-t-butylsalicylate: 0.5 part by mass
Paraffin wax (highest endothermic peak temperature: 78° C.): 5 parts by mass These materials were sufficiently mixed using a Henschel mixer (FM-75J, manufactured by Nippon Coke & Engineering). The mixture was kneaded in a twin screw kneader (PCM-45, manufactured by Ikegai) set at a temperature of 130° C., with a feed rate of 60 kg/h (temperature of the mixture during extrusion was about 150° C.). After being cooled, the resulting mixture was crushed with a hammer mill, and further pulverized to much smaller particle sizes with a mechanical pulverizer (T-250, manufactured by Turbo Kogyo) at a feed rate of 20 kg/h.

The finely pulverized toner powder was sized with a multi-classification classifier using the Coanda effect to yield toner (1).

The resulting toner (1) had a weight average particle size (D4) of about 6.0 μm, and included particles having a diameter of 4.0 μm or less with a percentage of 30.2% by number and particles having a diameter of 10.1 μm or more with a percentage of 0.6% by volume.

Examples 33 to 37

Toners (2) to (6) were produced in the same manner as in Example 32, except that compound (1) was replaced with the compound shown in Table 4.

Comparative Examples 7 and 8

Comparative toners (1) and (2) were produced in the same manner as in Example 32, except that compound (1) was replaced with comparative compounds (1) and (2), respectively.

Evaluations

Image samples were prepared using toners (1) to (6) and comparative toners (1) and (2). The image properties of the image samples were compared for evaluation as shown below.

Rating of Toner Chromaticity

The chromaticity of each sample was estimated as below. Samples of 16-step gradation images whose maximum toner amount was adjusted to 0.45 mg/cm$^2$ were produced under normal environment (temperature: 25° C., humidity: 60% RH) using a color copy machine modified CLC-1100 (manufactured by Canon, from which the fixing oil application mechanism was removed). For this operation, CLC color copy paper (manufactured by Canon) was used as the base paper of the image samples. For each of the resulting image samples, the color parameters (L*, a*, and b*) in the CIE L*a*b* color system were measured with a spectrophotometer SpectroLino (manufactured by Gretag Macbeth).

Color deviation α defined as below was calculated using chromaticity parameters a* and b* at L*=60.

$$\alpha = |b^*/a^* - 1.5|$$

A: α was less than 0.20 (close to orange color).
B: α was in the range of 0.20 to less than 0.50 (rather close to orange color).
C: α was 0.50 or more (different from orange color).

Rating of Toner Light Fastness

For evaluation of toner light fastness, an image forming apparatus (hereinafter referred to as LBP) modified from LBP-5300 (manufactured by Canon) was used. More specifically, LBP-5300 was modified by replacing the developer blade in the process cartridge (hereinafter referred to as CRG) with an 80 μm-thick SUS blade. Furthermore, the printer was modified so that a developing bias of −200 V was able to be applied to the blade. For evaluation, GRGs charged with respective yellow toners were prepared for each test. Each CRG charged with a toner was set to the LBP for evaluation. Each image sample was exposed to an environment of an illuminance of 340 nm at 0.39 W/m$^2$ and at a temperature of 40° C. and a relative humidity of 60% for 25 hours in a xenon test apparatus Atlas Ci 4000 (manufactured by Suga Test Instruments). The reflected density of the printed image was measured before and after the exposure test. The color difference ΔE was defined as below using initial color parameters $a_0^*$, $b_0^*$, and $L_0^*$ and color parameters a*, b*, and L* after exposure:

$$\Delta E = \sqrt{(a^* - a_0^*)^2 + (b^* - b_0^*)^2 + (L^* - L_0^*)^2}$$

The rating criteria were as follows. When ΔE after 25 hours was less than 10, the light fastness of the sample was determined to be good.

A: ΔE<6 (excellent light fastness)
B: 6≤ΔE<10 (good light fastness)
C: 10≤ΔE (poor light fastness)

TABLE 4

| Compound used | Use | a* | b* | α | Rating | ΔE after 25 h | Light fastness rating |
|---|---|---|---|---|---|---|---|
| Example 32 | Compound (1) | Toner (1) | 58.2 | 100 | 0.22 | B | 5.90 | A |
| Example 33 | Compound (3) | Toner (2) | 58.1 | 104 | 0.29 | B | 5.70 | A |
| Example 34 | Compound (11) | Toner (3) | 60.4 | 102 | 0.19 | A | 9.20 | B |
| Example 35 | Compound (14) | Toner (4) | 57.0 | 105 | 0.34 | B | 8.20 | B |
| Example 36 | Compound (22) | Toner (5) | 57.2 | 103 | 0.30 | B | 6.30 | B |
| Example 37 | Compound (15) | Toner (6) | 63.9 | 102 | 0.10 | A | 6.90 | B |
| Comparative Example 7 | Comparative Compound (1) | Comparative toner (1) | 50.2 | 109 | 0.67 | C | 7.60 | B |
| Comparative Example 8 | Comparative Compound (2) | Comparative toner (2) | 63.3 | 61.0 | 0.54 | C | 23.10 | C |

As clearly shown in Table 4, the toners using a compound having the structure expressed by general formula (1) have a more lightfast orange color than the comparative toners using the comparative compounds.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2015-085299, filed Apr. 17, 2015, which is hereby incorporated by reference herein in its entirety.

What is claimed is:

1. A compound having represented by formula (1):

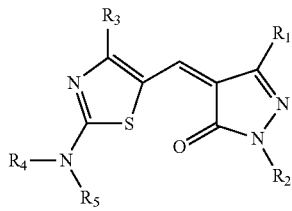

wherein $R_1$ represents a group selected from the group consisting of alkyl group, aryl group, aryl group having a substituent, acyl group, carboxy group, alkoxycarbonyl group, carboxamide group, and cyano group; $R_2$ represents a group selected from the group consisting of alkyl group, aryl group, and aryl group having a substituent; $R_3$ represents alkyl group group; and $R_4$ and $R_5$ each independently represent alkyl group, and
wherein the substituents of $R_1$ to $R_2$ are each one selected from the group consisting of alkyl group, alkoxy group, and sulfonic acid salt group.

2. An ink containing the compound as set forth in claim 1.

3. A color filter resist composition containing the compound as set forth in claim 1.

4. A thermal transfer recording sheet containing the compound as set forth in claim 1.

5. A toner containing the compound as set forth in claim 1.

6. The compound according to claim 1, wherein $R_1$ represents methyl group.

7. The compound according to claim 1, wherein $R_3$ represents tert-butyl group.

8. The compound according to claim 1, wherein both $R_4$ and $R_5$ represents 2-ethylhexyl group.

9. The compound according to claim 1, wherein
$R_1$ represents methyl group;
$R_3$ represents tert-butyl group; and
both $R_4$ $R_5$ represent 2-ethylhexyl group.

* * * * *